(12) United States Patent
Cornacchio et al.

(10) Patent No.: US 8,337,440 B2
(45) Date of Patent: Dec. 25, 2012

(54) REDUCED DENSITY FOAM FOR USE IN SURFACES OF ORTHOTICS

(76) Inventors: Kevin Cornacchio, Buffalo, NY (US); Michael Malaga, San Francisco, CA (US)

(*) Notice: Subject to any disclaimer, the term of this patent is extended or adjusted under 35 U.S.C. 154(b) by 342 days.

(21) Appl. No.: 12/829,476

(22) Filed: Jul. 2, 2010

(65) Prior Publication Data
US 2011/0004137 A1    Jan. 6, 2011

Related U.S. Application Data

(60) Provisional application No. 61/300,926, filed on Feb. 3, 2010, provisional application No. 61/223,205, filed on Jul. 6, 2009.

(51) Int. Cl.
*A61F 5/00* (2006.01)
(52) U.S. Cl. ............................................. 602/19; 602/8
(58) Field of Classification Search .................. 602/3–5, 602/8, 16, 20–30; 128/877–879, 882
See application file for complete search history.

(56) References Cited

U.S. PATENT DOCUMENTS

| | | | |
|---|---|---|---|
| 4,832,010 A | 5/1989 | Lerman | |
| 5,578,260 A | 11/1996 | DeSena | |
| 5,720,915 A | 2/1998 | Joppen | |
| 5,796,620 A | 8/1998 | Laskowski | |
| 2004/0133431 A1* | 7/2004 | Udiljak et al. | 705/1 |
| 2005/0112397 A1 | 5/2005 | Rolfe | |
| 2005/0212166 A1 | 9/2005 | Seo | |
| 2006/0277772 A1* | 12/2006 | Pupko | 33/3 R |
| 2011/0208100 A1* | 8/2011 | Eck et al. | 602/21 |

* cited by examiner

*Primary Examiner* — Michael A. Brown
(74) *Attorney, Agent, or Firm* — Jennifer Meredith, Esq.; Fariba Sirjani, Esq.; Meredith & Keyhani, PLLC

(57) ABSTRACT

Method and device for tailoring the density of a compressible, non-rebounding foam used in capturing anatomical impressions to account for the variations in body weights and sizes, the foam fabricated by the method or device and the custom surface fabricated using the foam. The device is configurable to create a wide range of densities suitable for a wide range of body types. The resulting imprinted foams are then encased in hard surfaces to obtain a mold that provides support surfaces for the back and buttocks in the construction of custom molded chairs, seat cushions and back orthotics. The reduced density foam is suitable for fabrication of orthotics that fit to large areas of the body.

11 Claims, 20 Drawing Sheets

100

23

511

512

911

912

913

1000

Using foam to take the impression of a subject using a wheelchairs

The subject is lowered into the L-shaped foam and an impression is taken which can vary with the height and posture of the subject. The foam could extend to capture the cervical and cranial imprint. A correspondingly tall wheelchair would be needed to received the mold.

Subject rests a portion of their leg onto the foam and the leg is then pressure into the foam to take an impression.

Using foam to create impression of aircraft or automobile seat

The foam is pressed against the face of the unfinished seating apparatus of the plane or automobile, making a mirror image which can then be over-sprayed in the same manner as mold taken from the human body Irregular geometry of the seat backing to be accommodated by the foam

REDUCED DENSITY FOAM FOR USE IN SURFACES OF ORTHOTICS

CROSS-REFERENCE TO RELATED APPLICATIONS

The present application claims priority to and the benefit of U.S. Provisional Patent Applications No. 61/300,926, filed at the U.S. Patent and Trademark Office on Feb. 3, 2010, and No. 61/223,205, filed at the U.S. Patent and Trademark Office on Jul. 6, 2009, the entire content of both of which is incorporated by this reference.

FIELD OF THE INVENTION

The present invention pertains generally to the field of orthotics including form-fitting chairs, seat cushions, back orthotics, anatomical support surfaces, and, more particularly, to the manufacture, adaptation, and coating of foams used in custom chairs and orthotics.

DESCRIPTION OF RELATED ART

Obtaining a seating support structure that conforms to a seated person's body has been a goal of seating designers for decades. Multiple techniques have been employed to make adjustments to task chairs to add lumbar support, tilt the seat pan, rotate the pelvis, or even out pressure on the buttocks. All of these techniques aim to conform to a person's anatomy by means of levers and controls. Ideally, one would be able to take a direct impression of a person's back and buttocks and incorporate that impression into a custom chair, seat cushion or back orthotic. This has been attempted for the wheelchair market (see, e.g., U.S. Pat. No. 7,220,376), but the process is expensive, time-consuming, and involves pre-selecting foam densities in advance. Further, the resulting impression requires creating negative, positive, and then again negative impressions to achieve a usable form using foam, liquid molding material, and plastic beads. Alternatively, a myriad of controls have been attempted to recreate a custom molding result (see U.S. Pat. No. 7,140,057).

U.S. Pat. No. 7,220,376 explains that there are a number of sophisticated methods and devices available for use to determine and capture anatomical shapes. One type of device is a seating simulator. A seating simulator uses a relatively large chair-like structure in which flexible bags or containers of beads are confined. The user is seated on the bags and the beads distribute themselves around the user's anatomy. A vacuum is then applied within the bags, and the exterior pressure on the bags forces the beads to hold the conforming position. The user is then removed, and the user's shape is captured. Adjustments are thereafter made. To translate the captured shape into information which can be used to create the custom cushion, relatively sophisticated electronic mapping equipment is moved over the shape held by the bag. A multiplicity of different points across the shape are measured, and the measurements are transferred electronically to a software computational algorithm or program which defines a mathematical simulation of the captured shape of the user's anatomy. This simulation is thereafter used to create a mold from which the cushion is formed. Alternatively, a plaster or other material casting is made of the captured shape directly from the bag while the captured shape is held. The casting is shipped to a cushion manufacturer for interpretation and fabrication of a custom cushion having the desired support contour.

Another type of shape-capturing device uses a two-dimensional grid of plungers or rod-like elements which are brought into contact with the user's anatomy. The relative displacement or movement of the plungers due to contact with the anatomy is measured. The measurement data is then transferred electronically and is used by a computational algorithm or program which defines a mathematical simulation of the captured shape. Thereafter, the simulation is used to create a mold from which the cushion is formed.

The conventional methods and devices used for fabrication of custom chair surfaces suffer from various shortcomings. As mentioned above, the time and expense of the custom fitting process are high and replacing the custom fitted cushion needed to accommodate changes in the individual's physical characteristics is difficult. Some of the limitations of the prior art are found with respect to requirements for airtight casings, pneumatic equipment, and temperature sources and controls. Certain conventional methods and devices are used to fabricate chairs with extensive adjustments and moving parts which are subject to failure and inconvenience.

SUMMARY OF THE INVENTION

Aspects of the present invention address the issues associated with the conventional methods and devices of fabricating custom molded orthotics and the products that are the results of such methods and devices.

Aspects of the present invention provide methods and devices for tailoring the density of a compressible, non-rebounding foam, that is used in capturing anatomical impressions, to account for the variations in body weights and sizes. The aspects of the present invention also provide a foam fabricated by the method or device of the invention and a custom surface fabricated using the foam.

The method, device and the resulting foam of the aspects of the present invention are unique in that the foam is machined to lower its density to an appropriate level for the type of support surface being created and the size, weight, and shape of the individual who is using the foam. The pressure sensitive foam used by the aspects of the present invention is lightweight. Therefore, it may be transported via commercially available air in a cost effective manner. The foam may also be transported via ground transportation because it does not decay or degrade as a result of time. Further, this foam is resistant to decay and degradation when exposed to wide changes in temperature and humidity that would be experienced during transport or use in household, automotive, health care, aviation, or office environments.

The method of taking the individual impression, as provided by the aspects of the present invention, is unique in that it is cost effective, easy to accomplish, and may be performed without chemical, mechanical, or pneumatic devices. The resulting foam will hold its form for many years and can be replaced easily.

Aspects of the present invention provide a device for creating a required density in a molding foam. The device includes a jig plate, punches, a stripper plate, a back plate and an assembly or frame to integrate these and other components. The jig plate may be actuated by a number of different mechanisms such as pneumatic, hydraulic, manual, or electro-dynamic. The jig plate may be instrumented with a number of punches that are attached to the jig plate and is used to core out a pattern of depressions on the molding foam. Each punch may be individually connected to the jig plate and may vary in length or cross-section. For example, the cross section of the punches may be circular, elliptical, square, hexagonal, or rectangular. Each jig plate may be configured with punches that have the same cross section or a combination of different cross sections. The corresponding stripper plate is machined to correspond to the resulting matrix of punches and to conform to the cross section of the punches used. The punching of the foam may be accomplished with a number of punching processes. Each punching process may utilize punches of different cross section such that the combination of processes leaves the foam with matrices of holes that have different shapes. The molding foam is positioned below the stripper plate and is able to be configured with various thicknesses of foam. The depths of the punches are also configurable separately for each punch by means of controlling the jig plate actuator. A support structure that holds the stripper plate, the jig plate and the foam in place is configured with an actuator mechanism that extends and retracts the jig plate and attached punches. The actuator can be manual, pneumatic, hydraulic, electro-dynamic, or a number of other actuating types. The actuator presses the jig plate down upon the foam through the stripper plate matrix and is subsequently withdrawn to create a corresponding matrix of holes in the foam. This process can be repeated a number of times to obtain the required density of the molding foam. The stripper plate functions as an anchoring device for the foam and allows the punches to be withdrawn without deforming the foam.

Aspects of the present invention also provide a density reduced casting foam.

Aspects of the present invention also provide the taking of the subject's impression using the density reduced casting foam.

Aspects of the present invention also provide casting of a molded impression into a custom seat cushion, custom chair or a custom back orthotic. The support surfaces formed by this method can also be adapted by creating a perforated pattern in the surface intended to be placed in contact with the user. An appropriate number of holes can be made along the sides of the surface to allow ventilation or allow connection to a device that can circulate air within the cushion and through the perforation to reduce heat and moisture build-up. This adaptation is useful in the prevention and treatment of pressure ulcers.

Aspects of the present invention provide a device for machining of a reduced density foam suitable for orthotics. The device includes an assembly frame, an actuator supported on the assembly frame, and a jig plate coupled to the actuator and controlled by the actuator, the jig plate including punches for making holes in a piece of foam. The formation of the holes corresponding to the punches in the piece of foam yields the reduced density foam, and number and size of the holes are determined according to material of the piece of foam, requirements of the orthotics and dimensions and weight of a user being fitted with the orthotics.

Aspects of the present invention provide a method for fabrication of a custom fitted orthotic from a compressible non-rebounding foam. The method includes determining an amount of decrease in density of the foam, removing or compressing material from or in the foam to obtain a reduced density foam according to the amount of decrease determined, obtaining an impression of body parts of a user on the reduced density foam to obtain an imprinted foam, encasing the imprinted foam in a hard material for preserving a shape of the imprinted foam to obtain a molded foam, and incorporating the molded foam into the custom fitted orthotic for a subject user.

Aspects of the present invention provide a reduced density foam for use in a custom fitted orthotic. The reduced density foam is obtained from a process including selecting a piece of compressible non-rebounding foam according to a body part being custom fitted with the orthotic, determining an allowable reduction in density of the piece of foam according to weight and size of a user and purpose of the orthotic, removing material from the piece of foam according to a pre-determined pattern based on the allowable reduction to obtain a reduced density foam, impressing the reduced density foam with the body part of the user to obtain an imprinted foam, encasing the imprinted foam in a hard shell to preserve the custom fitted shape of the imprinted foam in a mold, and incorporating the mold in the custom fitted orthotic.

DETAILED DESCRIPTION OF THE INVENTION

Figure 1:
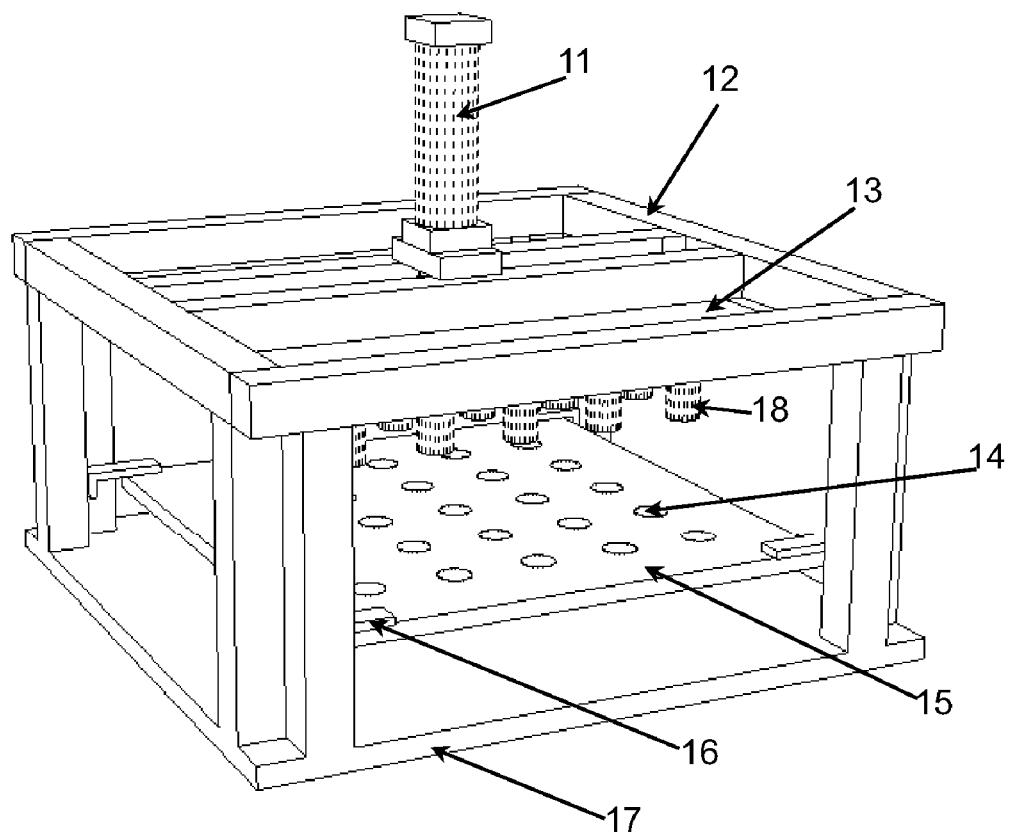
FIG. 1 is a perspective view of a device, according to aspects of the present invention, including a jig plate, a stripper plate, and an actuator assembled on an assembly frame and used for tailoring of the foam density.

A Aspects of the present invention provide methods and devices for tailoring the density of compressible, non-rebounding foam, which is used in capturing anatomical impressions of a user, to account for the variations in body weights and sizes. Aspects of the present invention also provide the foam fabricated by the methods or devices of the invention and the custom surface fabricated using the foam. The device is configurable to create a wide range of densities suitable for a wide range of body types. The resulting molds or castings are then encased in hard surfaces to provide support surfaces for the back and buttocks in the construction of custom molded chairs, seat cushions and back orthotics. The support surfaces formed by this method can also be adapted by creating a perforated pattern in the surface intended to be placed in contact with the user. A number of holes may be made along the sides of the surface to allow ventilation or allow connection to a device that can circulate air within the cushion and through the perforation to reduce heat and moisture build-up. This adaptation would be useful in the prevention and treatment of pressure ulcers.

Including the impression of a person's body in the cushion or orthotic reduces peak pressures on the person's back or buttocks by more evenly distributing the surface area in contact with the supporting surface. In addition, by directly molding the back and buttocks, the person's posture can be improved by supporting the correct pelvic tilt and lumbar position. Aspects of the present invention provide a technique for inexpensively and repeatably tailoring the pressure density of compressible, non-rebounding foam, encasing that foam in a rigid surface to preserve the contour, and then incorporating the contour into a chair, seat cushion, or back orthotic.

Due to differences in the body weight and surface area of anatomical surfaces, such as the back and buttocks, it is difficult to obtain a foam density that can be used in the vast variety of body type combinations. Aspects of the invention include a method and a mechanism to custom-tailor the density of a piece of compressible, non-rebounding foam to accommodate a wide range of body types and weights. The tailoring of the density of the molding foam leads to obtaining an accurate molding or casting of the anatomical form being molded and cast.

Further, in order to reduce cost and manufacturing time, aspects of the present invention describe a manner to encase the molding foam directly in a hard surface forming the underpinnings of a seat cushion or backrest of a custom chair, a seat cushion by itself, or of a back orthotic.

Moreover, in order to provide ventilation to limit heat and moisture buildup, aspects of the present invention describe a manner to create a perforated pattern in the surface intended to be placed in contact with the user.

The foam that is used may be a commercially available foam, such as BIO-FOAM™, marketed by the Smithers Bio-Medical Systems Company of Kent, Ohio. This foam has been developed for the use of making anatomical castings.

While compressible, non-rebounding foams have been used to take impressions of feet to form orthotics for shoes, their applicability to taking impressions of the rest of the body has been limited by their density. Reducing the density of the foam, according to aspects of the present invention, makes the foam suitable for other uses where the body part that is being fitted is larger than a foot, is more irregularly shaped, or has a lower pressure profile. In these cases the unmodified foam would be prohibitively dense and often too heavy.

While the following description makes references to a foam, other similar material that may be imprinted with an impression of the body of a user and are also amenable to a controllable reduction in their density by removal of some of the material.

FIG. 1 is a perspective view of a device, according to aspects of the present invention, including a jig plate, a stripper plate, and an actuator assembled on an assembly frame and used for tailoring of the foam density.

Tailoring of the foam density may be performed by a device 100 shown in FIG. 1. The device 100 includes an actuator 11 that is supported on an assembly frame 12. The actuator 11 is coupled to a jig plate 13. A stripper plate 15 is fastened in the assembly frame 12 and positioned in such a way as to be above a piece of subject foam.

The jig plate 13 contains a matrix of punches 18. The punches 18 are shown as cylindrical punches protruding from a surface of the jig plate 13. However, the punches may have various combinations of cross-sectional geometries.

The stripper plate 15 is machined to match the matrix of punches on the jig plate 13 such that the pattern cored out from the foam matches the matrix of punches on the jig plate and the corresponding matrix of holes in the stripper plate.

The jig plate 13 is adapted to move in a direction substantially parallel to the actuator 11 and is connected perpendicular to the plane of the jig plate. The motion of the jig plate 13 may be accomplished through extension of a piston in the actuator 11. The jig plate 13 is actuated and moved by the actuator 11 so that it impinges on the subject foam through the stripper plate 15.

The pressure on the actuator may be tailored for each punching operation or may even be varied during each punching operation. In the exemplary embodiment that is shown in FIG. 1, the foam is located below the stripper plate such that the foam may be held in place by the stripper plate. After punching, the jig plate 13 is withdrawn and the stripper plate 15 holds the foam in place so that the punches can be completely removed. The foam may be re-positioned and the punching process repeated to achieve the desired foam density.

In the embodiment described above, the stripper plate is used to ensure that the punches do not adhere to the foam. Other methods of insuring that the punches do not adhere to the foam during removal may include: using a lubricant on the punches, creating a vacuum below the foam to hold the foam in place during withdrawal, and polishing or grinding of the surfaces on the punch to insure uniformity. Methods that reduce friction between the punches and the foam or hold the foam in place allow withdrawal of the punches without deforming of the foam.

The jig plate may be withdrawn by the same actuator mechanism that provided the pressing force, or by another mechanism that is used to raise the jig plate. Mechanisms used for raising the jig plate include but are not limited to manual, pneumatic, hydraulic, or electro-dynamic.

The foam may be positioned in the cavity by a number of different methods, including manually, via conveyor, via vibrating screen, via gravity fed shoot, via a pneumatic arm, or via a ram. The foam can be removed from the cavity by one of the insertion methods or by a combination of the above methods. Other methods and mechanisms for producing the matrix of holes in the foam can include water jet forming, burning, boring, or cutting.

Figure 2:
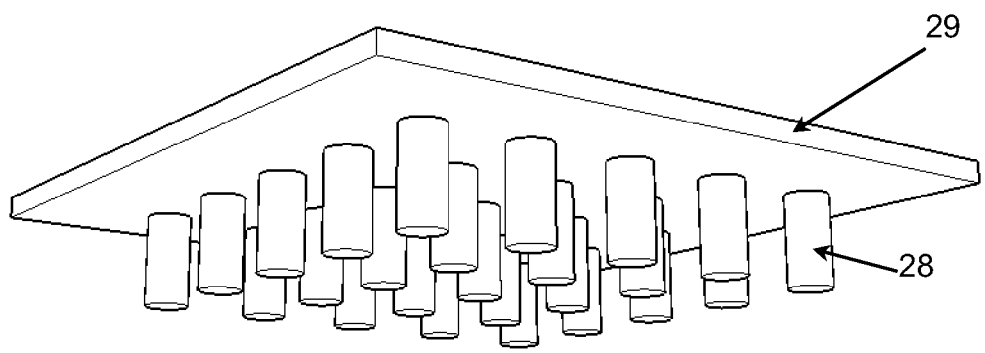
FIG. 2 is a perspective view of a jig plate including punches, according to aspects of the present invention.

FIG. 2 is a perspective view of a jig plate including punches, according to aspects of the present invention.

An exemplary jig plate 23 is shown with punches 28 protruding from a plate 29 of the jig plate 23 at substantially perpendicular angles. The punches 28 form a matrix of punches on the plate 29 of the jig plate 23.

The punches are shown as cylindrical protrusions. However, the shape of the punches 28 and the arrangement of the punches 28 on the plate 29 may be varied. All of the punches on a plate may have the same cross section. Alternatively, the punches on a plate may have different cross sections such that the same jig plate produces, for example, both circular and rectangular holes in the foam being punched during the same punching operation.

Further, the punches 28 and the plate 29 may be fabricated from one piece of material or they may be fabricated separately and coupled together via various means.

In one embodiment, the jig plate 23 is used in the device 100 of FIG. 1.

Figure 3:
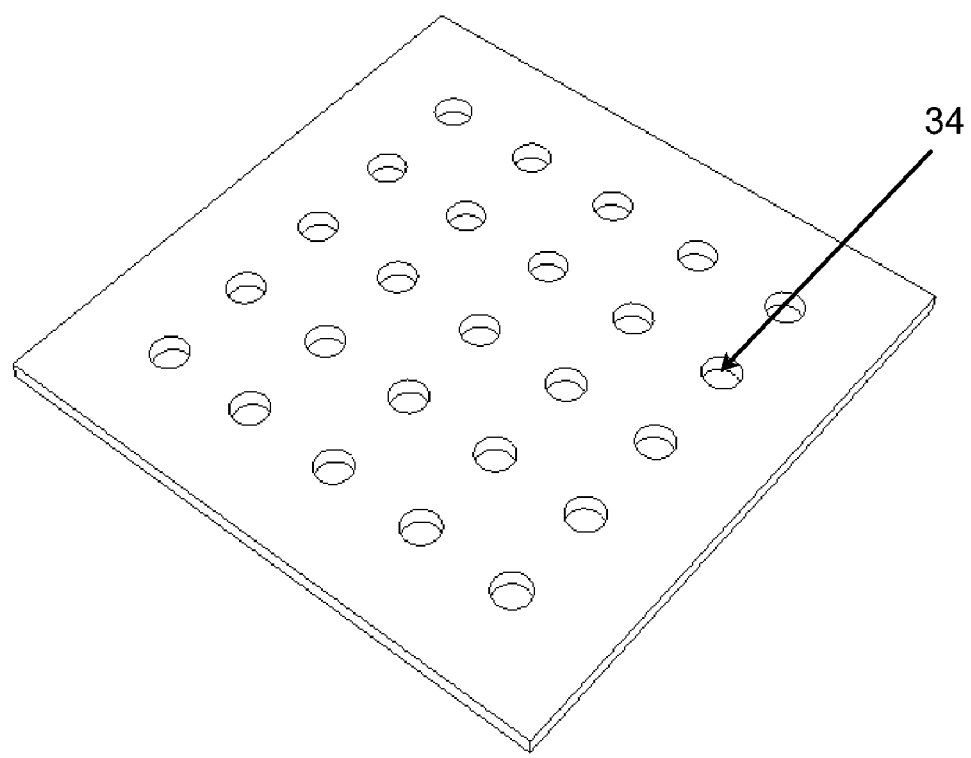
FIG. 3 is a perspective view of a stripper plate, according to aspects of the present invention.

FIG. 3 is a perspective view of a stripper plate, according to aspects of the present invention.

An exemplary stripper plate 35 is shown in FIG. 3. This stripper plate may be used in device 100 of FIG. 1. The stripper plate 35 includes a matrix of openings 34 that are fabricated to match the punches on the jig plate. In the exemplary embodiment shown in FIG. 1, when the device is operational, the punches of the jig plate are driven through openings of the stripper plate and then through the foam located under the stripper plate.

Figure 4:
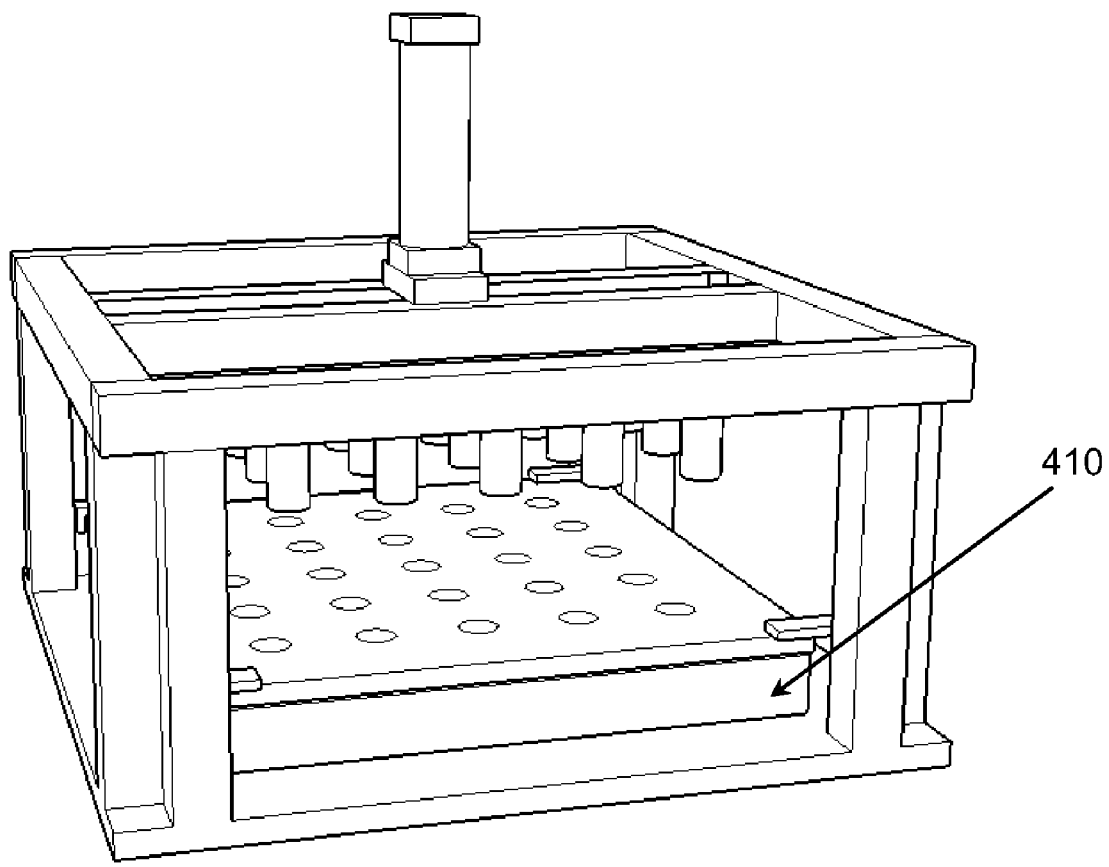
FIG. 4 is a perspective view of an assembly frame, with the molding or casting foam inserted, according to aspects of the present invention.

FIG. 4 is a perspective view of an assembly frame, with the molding or casting foam inserted, according to aspects of the present invention.

A molding foam 410 is shown as located under the stripper plate in FIG. 4. For a different arrangement of components, the location of molding or casting foam may be different.

Figure 5:
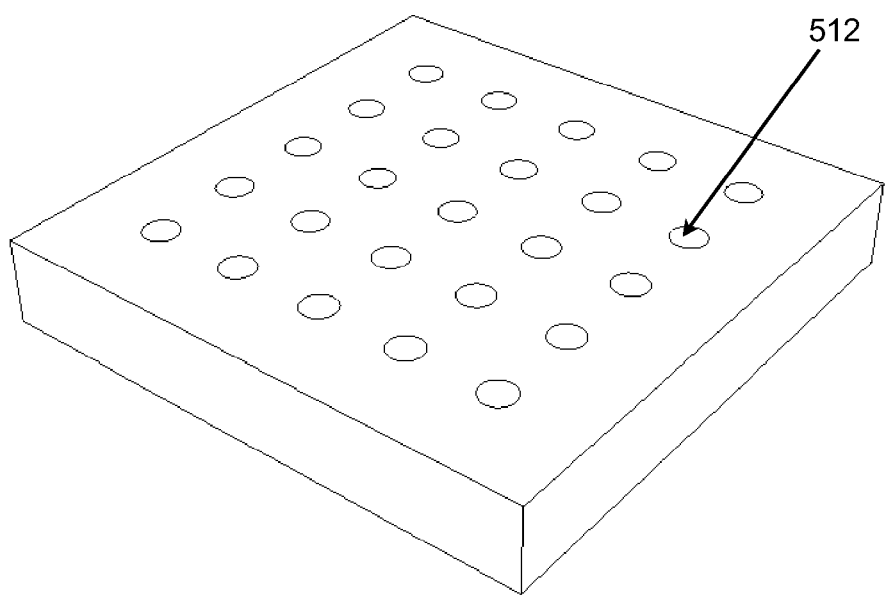
FIG. 5 is a perspective view of a casting foam that is cored to obtain a cored foam, according to aspects of the present invention.

FIG. 5 is a perspective view of a cored foam, according to aspects of the present invention.

A piece of cored foam 511, according to aspects of the present invention, is shown that may have been cored using the device 100 of the aspects of the invention. The foam 511 includes cored areas 512 that have been punched out by the coring device.

The foam used is a compressible, non-rebounding foam that may be used for casting and molding. Many of the types of foams that provide those qualities are marketed commercially for obtaining anatomical impressions. The foam is inserted into the coring device. The actuator causes the jig plate to impinge on the foam through the stripper plate with a pressure profile that is controlled to be either constant or varying. The jig plate is inserted to the required depth and then withdrawn. The foam is subsequently removed or can be re-cored with the same jig plate by repositioning the foam or with a combination of different jig plate punch matrices. The depth and pressure profile can be tailored independently for each punching operation. The foam is then removed by one of the above described processes or a similar process. The cored foam can then be cleaned, coated with a protective layer of porous or non-porous material and then sealed.

Figure 6:
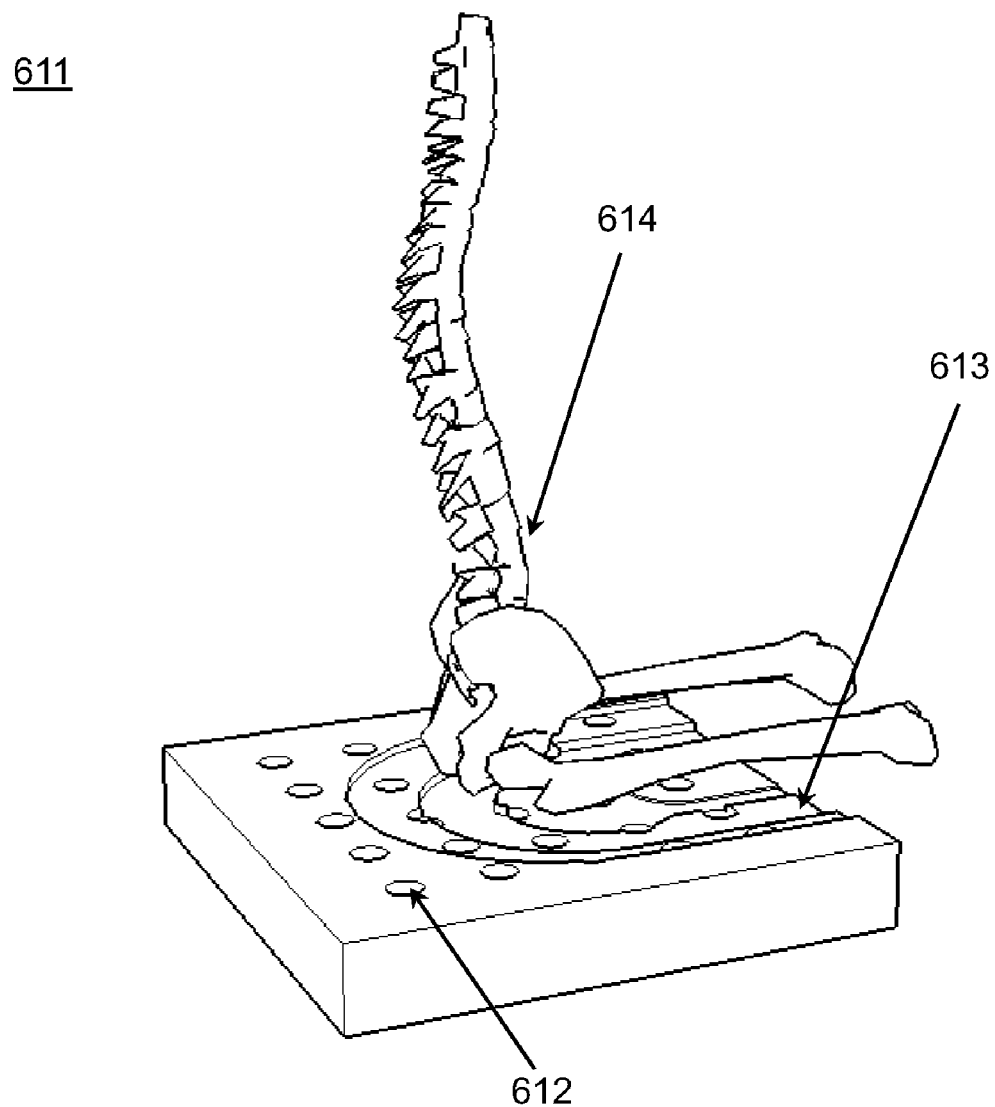
FIG. 6 is a perspective view of the positioning of a user on the cored foam for creating an impression of the buttocks in the cored foam, according to aspects of the present invention.

FIG. 6 is a perspective view of the positioning of a user on the cored foam for creating an impression of the buttocks in order to obtain an imprinted foam, according to aspects of the present invention.

A cored and imprinted foam 611 is shown that includes holes 612 and contours 613. The holes may have been cored out of the foam using a device such as the device 100 of FIG. 1. The contours are imprinted onto the cored foam by the pressure exerted by the body of a user 614 that is placed over the foam 611.

Figure 7:
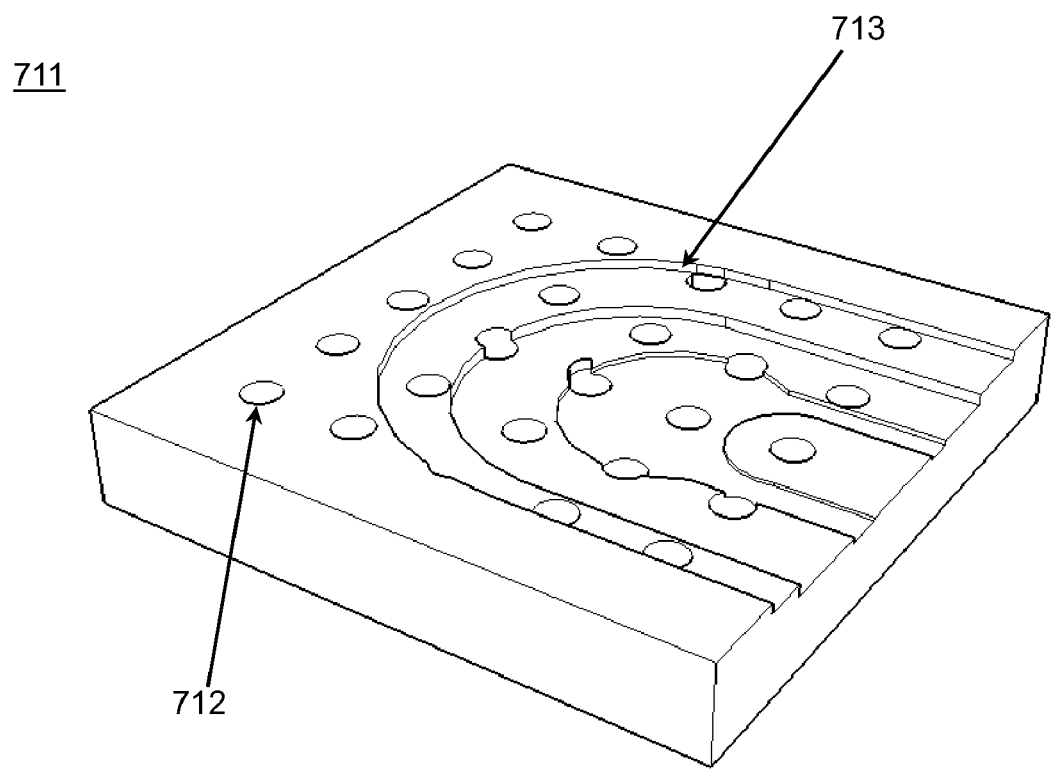
FIG. 7 is a perspective view of an imprinted foam after a buttocks imprint, according to aspects of the present invention.

FIG. 7 is a perspective view of an imprinted foam after a buttocks imprint has been obtained, according to aspects of the present invention.

Imprinted foam 711 includes holes 712 and contours 713. The imprinted foam 711 is fabricated from a piece of cored foam after being imprinted by the pressure from the body of a user. The contours 713 form an imprint of the buttocks and thighs that pressed the cored foam into its current shape reflected in the imprinted foam 711.

Figure 8:
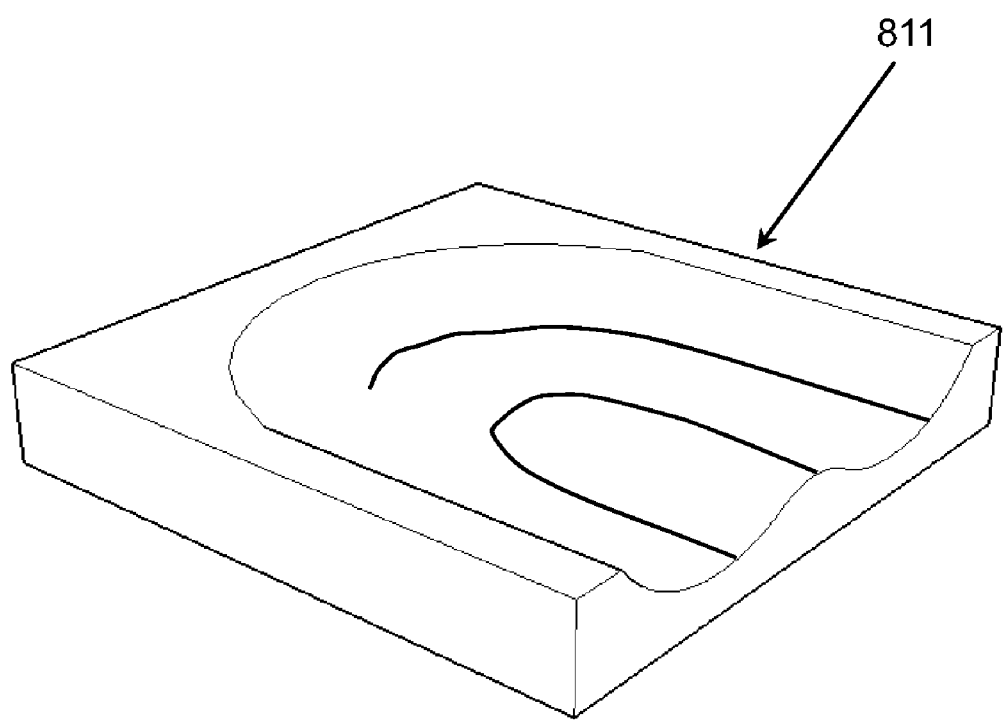
FIG. 8 is a perspective view of an coated foam obtained after coating of an imprinted foam with a hard substance, according to aspects of the present invention.

FIG. 8 is a perspective view of an coated foam obtained after coating of a cored and imprinted casting foam with a hard substance, according to aspects of the present invention.

The imprinted foam 711 generated in FIG. 7 is next transformed into a casting or a mold that holds its shape. In order to transform the casting foam into a mold, the imprinted foam 711 is sprayed, or otherwise coated, with a hard substance. FIG. 8 shows a mold 811 that is generated as a result of this process of coating the imprinted cored casting foam with a hard substance or a substance that hardens after being sprayed. An example of this process using fiberglass starts with the mold being first sealed to insure that the foam does not absorb a resin. A spray gun then deposits the resin and chop, or glass fibers, onto the treated casting foam. Once the material is sprayed onto the foam, rollers are used to flatten down the glass fibers to ensure a smooth surface and ensure that the fibers are fully encapsulated in the resin. The form is then cured into a hardened surface. Another exemplary method includes a vacuum forming process. In this process, a sheet of plastic is heated and then lowered down upon the mold. Both the mold and the heated plastic sheet are then subjected to a partial vacuum to allow the plastic to fully conform to the mold. The resulting mold is cooled to allow the plastic to harden.

Other methods of preserving the shape of the imprinted foam may also be used to obtain the mold.

Figure 9:
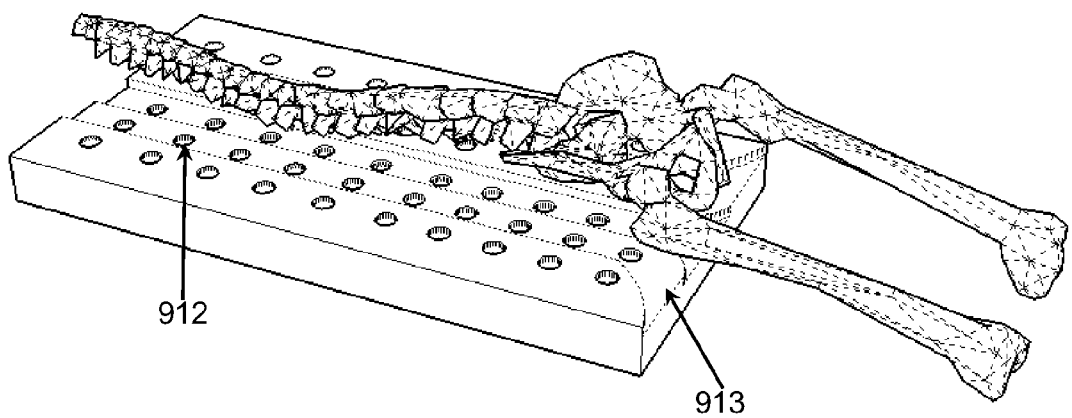
FIG. 9 is a perspective view of the positioning of the person on the cored foam for creating the impression of the back, according to aspects of the present invention.

FIG. 9 is a perspective view of the positioning of the person on the cored foam for creating the impression of the back, according to aspects of the present invention.

In FIG. 9 another cored and imprinted foam 911 is shown that includes holes 912 and contour imprints 913. The contour imprints 913 are formed by the pressure from the back of a person lying on the cored foam and reflect the contours matching the back of this person.

Figure 10:
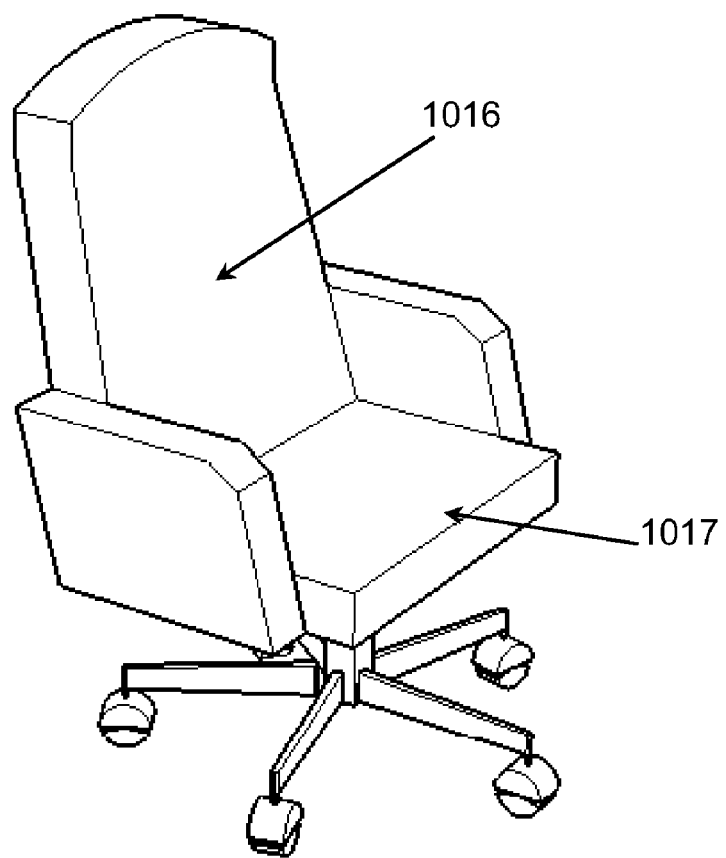
FIG. 10 is a perspective view of an office chair with the seat and back cushions constructed with upholstered molds of foam, according to aspects of the present invention.

FIG. 10 is a perspective view of an office chair with the seat and back cushions constructed with upholstered molds of foam, according to aspects of the present invention.

A chair 1000 is shown whose back cushion 1016 and seat cushion 1017 are made from molds that fit the back and buttocks of an individual user. The back cushion 1016 and the seat cushion 1017 may correspond to the cored and imprinted casting foam 911 and the imprinted foam 711 after having been coated with a material that allows the foam to hold its shape.

As the above drawings show, when a person such as a patient in need of custom molded orthotics is positioned on the foam, as in FIG. 6, the foam compresses a desired distance and does not rebound, thus leaving an impression of the buttocks, as shown in FIG. 7, or of the back, as shown in FIG. 9. The foam is then coated with resin and a fiberglass chop or a vacuum-formed plastic coating, resulting in a hard surface, as shown in FIG. 8. This hard surface is then covered with standard upholstery foam, upholstered and attached to a chair frame, as shown in FIG. 10. The seat cushion 1017 has a custom-formed mold of the person's buttocks and the backrest 1016 has a custom formed mold of the person's back.

In the case of the back orthotic or free-standing seat cushion a mechanism is attached to the device to allow it to be affixed to a wheelchair, vehicle or aircraft seat, or another other stationary chair. This may be accomplished by means of straps, hooks, adhesive fasteners, hook-and-pin tape (e.g. Velcro) or a similar method. Alternatively, the device may be used without a fastening device.

Figure 11:
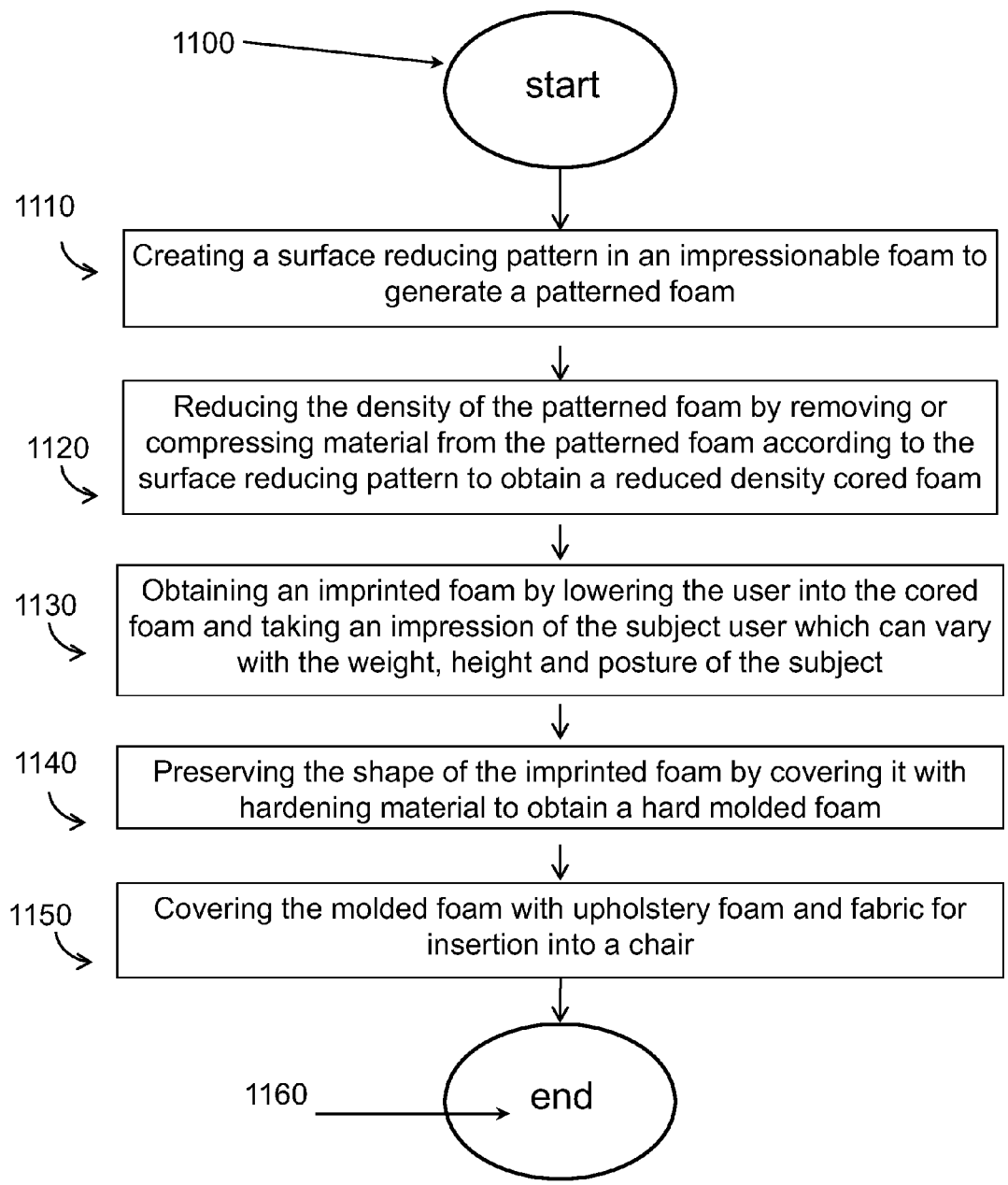
FIG. 11 shows a flowchart of a method of fabrication of a custom mold, according to aspects of the present invention.

FIG. 11 shows a flowchart of a method of fabrication of a custom mold, according to aspects of the present invention.

Aspects of the present invention provide a method for creating orthotics and other apparatuses that are custom-formed and custom-molded to minimize peek pressures that form between portions of the human body and various support surfaces. Such orthotics include beds, chairs, automobile seats, aircraft seats, pressure wound prevention and treatment devices, and wheelchairs. The orthotics also provide for the correct positioning of the pelvis while seated. The orthotics can be used as standalone devices to interface with standard support surfaces, or can be built into a chair, bed, or other custom support surface. One of the applications of the aspects of the present invention is the manufacture of custom chairs whereby a seat pan or backrest is created from, or is designed and built to accept, an orthotic formed by the individual's buttocks and thighs, and the upper portion of the chair is formed by, or is designed and built to accept, an orthotic formed by the individual's back.

One exemplary method by which the orthotic is fabricated is shown in FIG. 11.

The method begins at 1100.

At 1110, a honeycomb or other surface reducing pattern is machined into a compressible, non-rebounding foam to obtain a patterned piece of foam.

At 1120, to reduce the density of the foam, some of the foam material is extracted from the patterned foam and a cored foam is obtained. Alternatively, some of the foam material may be compressed into the foam to obtain a reduced surface foam.

Removing the machined portions from the foam material adjusts the surface area of the foam that comes into contact with the individual being fitted. Removal of the machined material also reduces the density of the piece of foam. After the foam is machined to an appropriate density to accommodate the size, weight, and portion of the body for which the orthotic is being creating, various fittings can be obtained. Compression of the machined material reduces the density of the surface of the piece of foam.

As mentioned above, while compressible, non-rebounding foams have been used to take impressions of feet to form orthotics for shoes, their applicability to taking impressions of the rest of the body has been limited by their density. Reducing the density of the foam, according to aspects of the present invention, makes the foam suitable for other uses where the body part that is being fitted is larger than a foot and the unmodified piece of foam would be prohibitively dense or heavy.

At 1130, a mold of the subject is taken by having the subject lie down or sit upon the reduced density cored foam and an imprinted foam is obtained. The impression of the subject user can vary with the weight, height and posture of the subject At 1140, the custom fitted section which forms the imprinted foam is over-sprayed with fiberglass or other hardening material to preserve the shape of the imprint and to create a molded foam or mold. The shape of the mold may be preserved by other methods that encase the custom fitted imprinted foam and turn it into a hard mold.

At 1150, the molded foam is covered with different materials such as upholstery foam and fabric to produce a custom fitted orthotic.

At 1160, the method ends.

The custom fitted orthotic can be replaced, as needed, over time should the subject's physical characteristics change. The molded portions of the orthotic can be replaced on the original chair. The modification of the original product is made cheaper and easier to transport due to the reduced size and weight of the shipped material.

Figure 12:
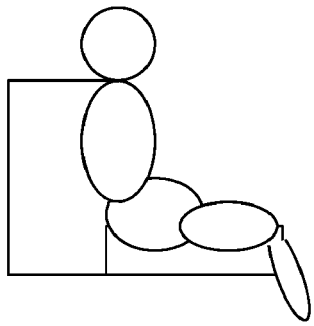
FIG. 12 shows one example of using an L shaped version of the casting foam to fit the buttocks and lower back of an individual who uses a wheel chair, according to aspects of the present invention.

FIG. 12 shows one example of using an L shaped version of the foam to fit the buttocks and lower back of an individual who uses a wheel chair, according to aspects of the present invention.

This method of FIG. 11 can also be applied to subjects with limited mobility, abnormal body shapes, and for users of wheelchairs by using an L-shaped, thicker foam which would take the impression of the area from the knees to the thoracic area of the spine as shown in FIG. 12. Similar techniques may be used to harden and cover the foam to match the particular assistive seating device in which they would spend much of their time.

Figure 13:
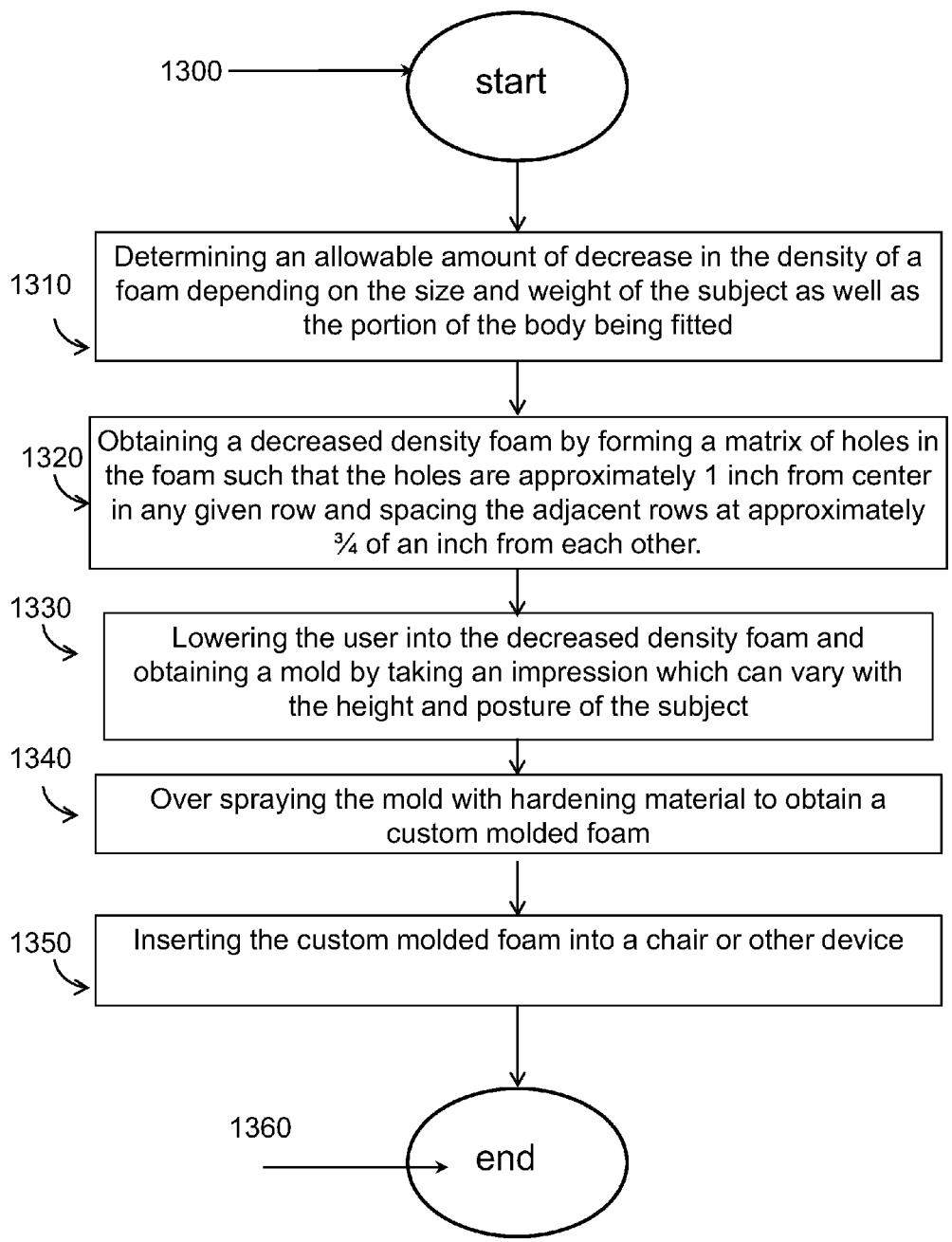
FIG. 13 shows a flow chart of a method for fabricating custom fitted orthotics from a form fitting foam, according to aspects of the present invention.
Figure 14:
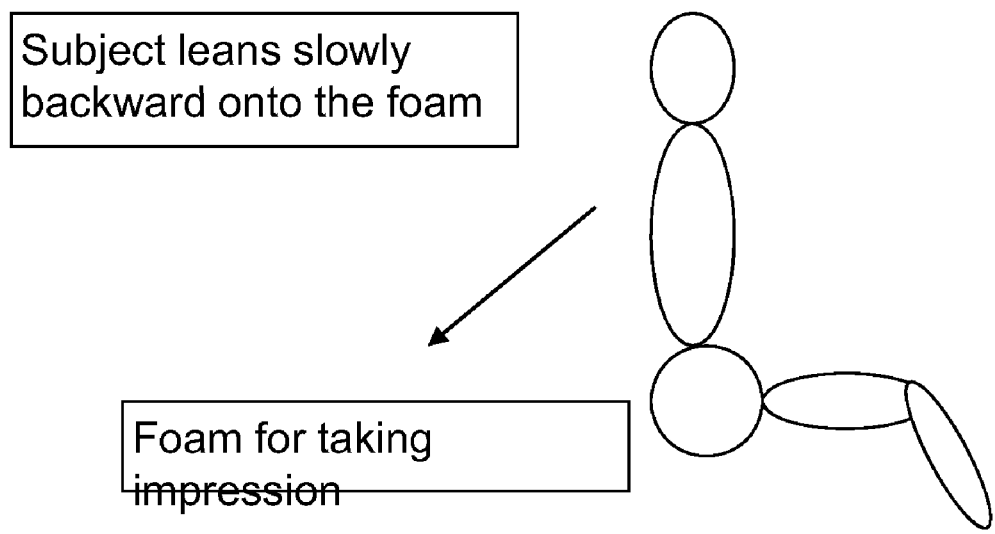
FIG. 14, FIG. 15, FIG. 16, and FIG. 17 show schematic drawings of various examples of placing the foam with respect to an individual user to form an impression of various portions of the body and to obtain an imprinted foam, according to aspects of the present invention.

FIG. 13 shows a flow chart of a method for fabricating custom fitted orthotics from a form fitting foam, according to aspects of the present invention.

FIG. 13 shows one exemplary method for fabricating custom fitted orthotics from a form fitting foam.

The method begins at 1310.

At 1320, an amount of decrease in the density of the foam is determined. The amount of allowable decrease depends on the size and weight of the subject as well as the portion of the body being fitted. A lower density foam is lighter and easier to body transport and handle. However, undue decrease in the foam density may compromise its integrity and utility.

At 1320, a matrix of holes is formed in the foam in accordance with the desired amount of decrease in the density and a decreased density piece of foam is obtained. In the example shown in FIG. 13, the matrix is such that the holes are approximately 1 inch from center in any given row and the adjacent rows are spaced at approximately ¾ of an inch from each other.

At 1330, a user, for whom the foam is being custom fitted, is lowered into the decreased density foam and an impression of the user is taken which can vary with the height and posture of the subject user. This taking of the impression yields a mold that fits the body of the user.

At 1340, the mold is over-sprayed with hardening material to obtain a custom molded foam that is custom imprinted with the contours of the body of the subject user.

At 1350, the custom molded foam is inserted into a chair or other orthotic device for use by the subject user. The custom molded foam is usually upholstered and fitted with other types of cushions before being used in a chair.

The method ends at 1360.

An exemplary device for creating the required density in the molding foam was shown in FIG. 1 and some of the ensuing drawings. The modification of the foam, the taking of the subject's impression, and the casting of the impression into a mold for use in a custom chair or back orthotic are schematically depicted in FIG. 14 through FIG. 20. FIG. 14 through FIG. 20 show schematic drawings that correspond to some of the steps of the flowcharts of FIG. 11 and FIG. 13.

FIG. 14, FIG. 15, FIG. 16, and FIG. 17 show schematic drawings of various examples of placing the foam with respect to an individual user to form an impression of various portions of the body and to obtain an imprinted foam, according to aspects of the present invention.

Figure 16:
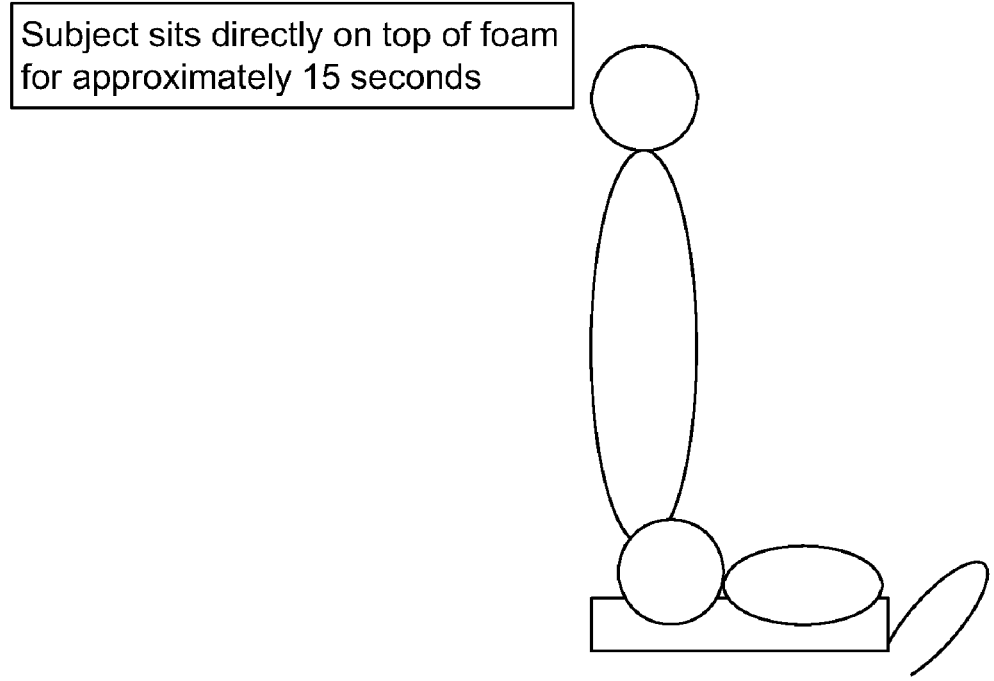
Figure 17:
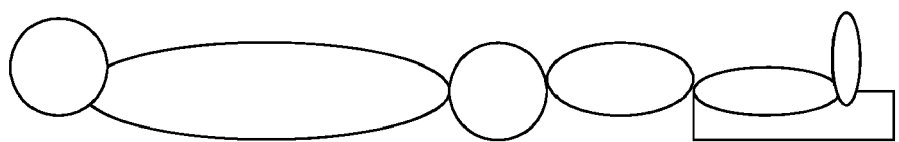

For example, in FIG. 16, for the taking of the subject's impression, the foam is placed on a hard surface, non-cored side down, providing equal support to the entire non-cored surface of the foam. The subject is positioned to allow for, in the case of a buttocks molding, the lowering of the subject onto the foam, with the entire buttocks and upper leg positioned in such a way that the entire surface of the subject's buttocks and upper leg is supported by the casting foam. The subject then lowers his/her body in such a way as to create an impression on the foam of the buttocks and upper leg with the entire weight of the subject's body being allowed to rest on the foam. The subject is supported in such a way that the pressure is in a perpendicular direction to the supporting surface, with the legs parallel to the supporting surface and the posture of the subject in a sitting position. The foam may or may not be anchored to the supporting surface. The supporting surface may or may not have attached arm supports or other supporting devices to allow for the positioning of the subject. For special purpose castings, the supporting surface may not be angled with respect to the ground. In such cases the legs may be positioned at an angle from parallel to the supporting surface. The resulting foam casting then retains the contours of the subject's buttocks and upper leg.

Figure 15:
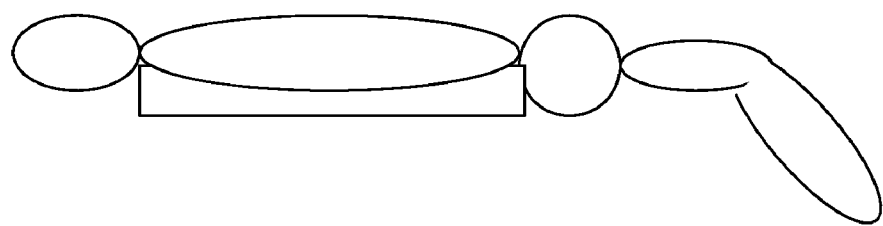

In a similar fashion, as shown in FIG. 15, the back of the subject may be molded into the casting foam. The foam is placed on a flat supporting surface. The subject sits on the supporting surface and is then supported in such a fashion as to allow the subject to recline upon the supporting foam. As the subject reclines, his buttocks impinges on the closest edge of the supporting foam to the subject and the back and upper buttocks is entirely supported by the casting foam. The supporting surface may or may not be parallel to the ground and the angle of the supporting surface may or not be adjustable during the casting process. The subject then arises from the support surface and foam through different methods allowing the subject to remove pressure from the casting foam. The resulting foam casting then retains the contours of the subject's back and upper buttocks.

The fitting process can be tailored to allow the subject to either remain in a stationary position during the process or to be adjusted from side to side to allow custom tailoring of the resulting contour.

Figure 18:
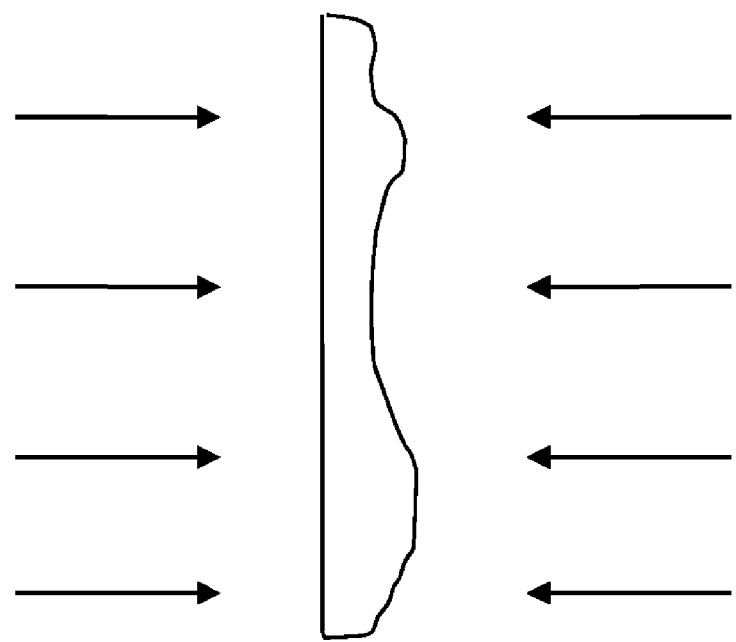
FIG. 18 shows a schematic drawing of over-spraying the imprinted foam to create a molded foam with a hard shell over which material can be fitted, according to aspects of the present invention.

FIG. 18 shows a schematic drawing of over-spraying the molded foam to create a hard shell over which material can be fitted, according to aspects of the present invention.

The molded impression is then hardened into a permanently formed contour of the impression using different processes to encase the mold in a hard shell. One method includes the application of a resin over the surface of the entire casting and a fiberglass chop sprayed over the resin. The chop is then processed to arrive at a smooth surface. The cast is cured to maintain the hardness of the surfaces. An alternate method can be the vacuum forming of a plastic coating onto the foam. The original foam may or may not be removed after this point, leaving the cast shell in fiberglass or other molding material.

Figure 19:
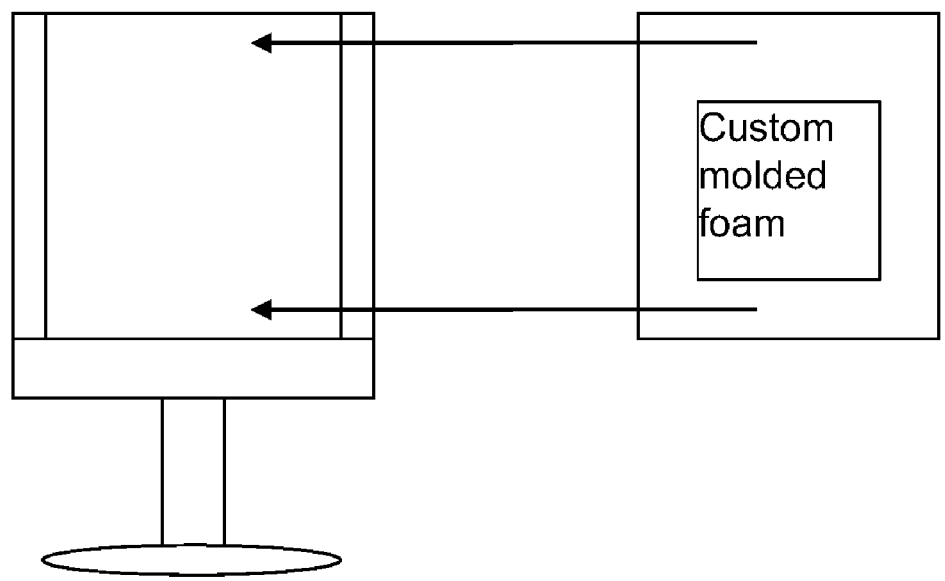
FIG. 19 shows a schematic drawing of fitting the molded foam into the receiving area of a custom chair, according to aspects of the present invention.
Figure 20:
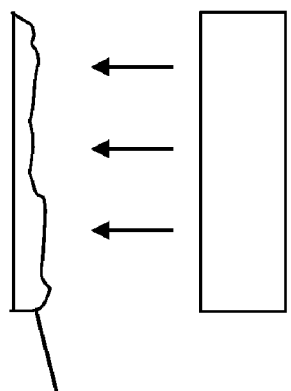
FIG. 20 shows a schematic drawing of fitting the molded foam to an existing hard back shell of an existing seat, according to aspects of the present invention.

FIG. 19 shows a schematic drawing of fitting the over-sprayed foam into the receiving area of a custom chair and FIG. 20 shows a schematic drawing of fitting the foam to an existing hard back shell of an existing seat, according to aspects of the present invention.

The resulting hardened mold may or may not be then attached to a wood or other hard insert on the base of the mold opposite to the contour. This insert may be made of a hard material, or may be a soft insert in cases where a soft material type is desired. The insert is positioned to come up against the hardened contour from the base direction. Depending on the depth of the insert, the shell is trimmed so that the rim of the shell is flush with the external surface of the insert. The insert may or may not be adhered to the shell through a variety of methods including staples, nails, and adhesives.

The supporting surface of the casting may then be coated with a variety of materials to provide a compressible and rebounding property, such as polypropylene foam or rubber. The insert is machined to receive a number of inserts or anchor bolts to allow the attachment of the object to the chair frame. This molded casting may be the seat pan, the chair back, a separate back orthotic or a freestanding seat cushion. In the case of the seat pan or chair back the object is affixed to the chair frame such that the seat pan is positioned to receive the buttocks of the subject and the chair back is positioned to receive the back of the subject. The chair frame is adjustable such that the chair back height can be positioned at a range of heights or angles and the seat pan can be positioned at an adjustable distance from the chair back and subsequently positioned with mechanisms on the chair frame. The support surfaces formed by this method can also be adapted by creating a perforated pattern in the surface intended to be placed in contact with the user. A number of holes can be made along the sides of the cushion to allow ventilation or connection to a device that can circulate air within the cushion and through the perforation to reduce heat and moisture build-up. This adaptation would be useful in the prevention and treatment of pressure ulcers.

The present invention has been described in relation to particular examples, which are intended to be illustrative rather than restrictive, with the scope and spirit of the invention being indicated by the following claims and their equivalents.

The invention claimed is:

1. A method for fabrication of a custom fitted orthotic from a compressible non-rebounding foam, the method comprising:
   determining an amount of decrease in density of the foam;
   removing or compressing material from or in the foam to obtain a reduced density foam according to the amount of decrease determined;
   obtaining an impression of body parts of a user on the reduced density foam to obtain an imprinted foam;
   encasing the imprinted foam in a hard material for preserving a shape of the imprinted foam to obtain a molded foam; and
   incorporating the molded foam into the custom fitted orthotic for a subject user.

2. The method of claim 1, wherein the amount of decrease in the density of the foam is determined responsive to size and weight of the subject, portion of body of the subject being fitted, and preventing compromise of integrity of the foam.

3. The method of claim 1, further comprising:
   forming ventilation holes into the molded foam.

4. The method of claim 1, wherein the removing or compressing of material from or in the foam includes:
   forming a matrix of holes in the foam according to the determined amount of decrease in the density,
   wherein the matrix includes holes substantially 1 inch from center in each row with adjacent rows being spaced at substantially ¾ of an inch from each other.

5. The method of claim 1, wherein the removing of the material from the foam is achieved by a method selected from machining a pattern of holes in the foam, or forming a pattern of holes in the foam by water jetting, burning, boring, or cutting.

6. The method of claim 1, wherein the removing of material from the foam includes punching holes in the foam during one or more punching operations, the method further comprising:
   tailoring punching pressure for each punching operation.

7. The method of claim 6, further comprising:
repositioning the reduced density foam after each punching operation for a subsequent punching operation to further reduce density of the reduced density foam.

8. The method of claim 1,
wherein the removing of material from the foam includes positioning of the foam in a punching assembly by an insertion method selected from manually, via conveyor, via vibrating screen, via gravity fed shoot, via a pneumatic arm, or via a ram, and
wherein the removing of material from the foam includes removing the reduced density foam from the cavity by one or a combination of the insertion methods.

9. The method of claim 1, further comprising:
cleaning the reduced density foam;
coating the reduced density foam with a protective layer of porous or non-porous material; and
sealing the reduced density foam.

10. The method of claim 1, further comprising:
covering the molded foam with upholstery foam and fabric to produce the custom fitted orthotic,
wherein the custom fitted orthotic is a seat cushion or backrest of a custom chair, a seat cushion by itself, or of a back orthotic.

11. The method of claim 1, further comprising:
forming holes along sides of the molded foam.

* * * * *